United States Patent [19]
Pamukcu et al.

[11] Patent Number: 6,046,199
[45] Date of Patent: Apr. 4, 2000

[54] METHOD OF INHIBITING NEOPLASTIC CELLS WITH TETRACYCLIC PYRIDO[3,4-B] INDOLE DERIVATIVES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/007,098

[22] Filed: Jan. 14, 1998

[51] Int. Cl.[7] ............... A61K 31/495; A61K 31/50
[52] U.S. Cl. ........................................... 514/250
[58] Field of Search ............................... 514/250

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/251 |
| 3,647,858 | 3/1972 | Hinkley et al. | 360/478 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,920,636 | 11/1975 | Takahasi et al. | 260/240 |
| 4,001,237 | 1/1977 | Partyka et al. | 260/256.4 B |
| 4,001,238 | 1/1977 | Partyka et al. | 260/256.4 B |
| 4,039,544 | 8/1977 | Broughton et al. | 260/256.4 F |
| 4,060,615 | 11/1977 | Matier et al. | 424/251 |
| 4,079,057 | 3/1978 | Juby et al. | 260/256.5 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/283 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/258 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/344 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,614,530 | 3/1997 | Kumar et al. | 514/293 |
| 5,614,627 | 3/1997 | Takase et al. | 544/293 |
| 5,859,006 | 1/1999 | Daugan | 514/250 |

FOREIGN PATENT DOCUMENTS

| | | | |
|---|---|---|---|
| 0 347146 A2 | 12/1989 | European Pat. Off. | C07D 471/04 |
| 0 349239 A2 | 1/1990 | European Pat. Off. | C07D 487/04 |
| 0 351058 | 1/1990 | European Pat. Off. | C07D 487/04 |
| 0 352960 A2 | 1/1990 | European Pat. Off. | C07D 473/30 |
| 0 395328 A2 | 10/1990 | European Pat. Off. | C07D 239/36 |
| 0 428268 A2 | 5/1991 | European Pat. Off. | |
| 0 463756 A1 | 1/1992 | European Pat. Off. | C07D 487/04 |
| 0 485157 A2 | 5/1992 | European Pat. Off. | C08B 37/08 |
| 0 485158 A2 | 5/1992 | European Pat. Off. | C08B 37/00 |
| 0 485171 A2 | 5/1992 | European Pat. Off. | C08B 37/08 |
| 0 485172 A2 | 5/1992 | European Pat. Off. | C08B 37/08 |
| 0 485173 A2 | 5/1992 | European Pat. Off. | C08B 37/08 |
| 0 508586 A1 | 10/1992 | European Pat. Off. | A61K 31/10 |
| 0 526004 A1 | 2/1993 | European Pat. Off. | C07D 487/04 |
| 0 607439 A1 | 7/1994 | European Pat. Off. | C07D 215/00 |
| 3038166 | 5/1981 | Germany . | |
| 274218 | 12/1989 | Germany | C07D 237/32 |
| 56-53659 | 5/1981 | Japan | C07D 233/88 |
| 57-167974 | 10/1982 | Japan | C07D 237/34 |
| 807826 | 1/1959 | United Kingdom . | |
| 2063249 | 6/1981 | United Kingdom | C07D 237/32 |
| WO 92/03419 | 3/1992 | WIPO | C07D 217/26 |
| WO 93/07149 | 4/1993 | WIPO | C07D 487/04 |
| WO 93/12095 | 6/1993 | WIPO | C07D 239/91 |
| WO 94/05661 | 3/1994 | WIPO | C07D 471/04 |
| WO 97/03985 | 2/1997 | WIPO | C07D 471/14 |

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology, vol. 24, pp. 83–87 (1983).
Federation Proceedings (1972) of the Federation of American Societies for Experimental Biology abstract Nos. 2044 and 2045.
Gilman, S.C. et al., Nonsteroidal Anti–inflammatory Drugs in Cancer Therapy, (circa 1985).
Brogden, R.N. et al., Drugs, vol. 16, pp. 97–114 (1978).
Hucker, H.B. et al., Drug Metabolism & Disposition, vol. 1, No. 6, pp. 721–736 (1973).
Shen, T.Y. et al., Chemical and Biological Studies on Indomethacin, Sulindac and Their Analogs, pp. 107–178 (circa 1975).
Duggan, D.E. et al., Clin. Pharm. & Therapeutics, vol. 21, No. 3, pp. 326–335 (1976).
Duggan, D.E. et al., J. Pharm. & Exper. Therap., vol. 201, No. 1, pp. 8–13 (1977).
Glavin, G.B. et al., Toxicology and Applied Pharmacology, vol. 83, pp. 386–389 (1986).
Moorghen, M. et al., Journal of Pathology, vol. 156, pp. 341–347 (1988).
Moorghen, M. et al., Acta Histochemica, Suppl.–Band XXIX, S. 195–199 (1990).
Bjarnason et al., Gastroenterology, vol. 94, No. 4, pp. 1070–1074 (1988).
Badrieh, Y., et al., Chem. Ber., vol. 125, pp. 667–674 (1992).
Silvola, J. et al., Effects of nonsteroidal anti–inflammatory drugs on rat gastric mucosal phosphodiesterase activity, Agents and Actions, vol. 12.4, pp. 516–520 (1982).

(List continued on next page.)

*Primary Examiner*—Jerome D. Goldberg
*Attorney, Agent, or Firm*—Robert W. Stevenson

[57] ABSTRACT

A method for inhibiting neoplastic, particularly cancerous and precancerous lesions by exposing the affected cells to pyrido[3,4b]indoles.

12 Claims, No Drawings

OTHER PUBLICATIONS

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

METHOD OF INHIBITING NEOPLASTIC CELLS WITH TETRACYCLIC PYRIDO[3,4-B] INDOLE DERIVATIVES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those of Formula I and solvates (e.g. hydrates) thereof, wherein:

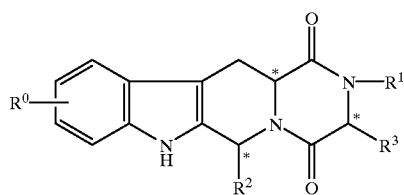

(I)

$R_0$ represents hydrogen, halogen or C1–6alkyl;

$R_1$ represents hydrogen or C1–6alkyl;

$R_2$ represents the bicyclic ring

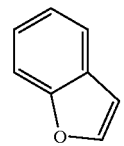

which may be optionally substituted by one or more groups selected from halogen and C1–3 alkyl; and $R_3$ represents hydrogen or C1–3alkyl.

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above. A particularly preferred subgroup of compounds useful in the present invention are compounds wherein $R_0$ represents hydrogen. A further preferred subgroup includes compounds wherein $R_1$ is selected from hydrogen, methyl and iso-propyl. Preferably, $R_2$ represents the unsubstituted bicyclic ring:

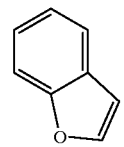

A still further subgroup of compounds of Formula I, are compounds wherein $R_3$ represent, hydrogen or methyl. The compounds of Formula I may contain one or more asymmetric centers and thus can exist as enantiomers or diastereoisomers. It is to be understood that the invention includes both mixtures and separate individual isomers of the compounds of formula (1). Particularly preferred are 6R and 12aR isomers.

Particular individual compounds useful in the methods of this invention include: (6R,12aR)-2,3,6,7,12,12a-hexahydro-6-(5-benzofuranyl)-2-methyl-pyrazino[2',1':6,1]pyrido[3,4-b]indole-1,4-dione; (6R,12aR)-2,3,6,7,12,12a-hexahydro-6-(5-benzofuranyl)-pyrazino[2',1':6,1]Pyrido[3,4-b]indole-1,4-dione; (3S,6R,12aR)-2,3,6,7,12,12a-hexahydro-6-(5-benzofuranyl)-3-methylpyrazino[2',1'-6,1]pyrido[3,4-b]indole-1,4-dione; (3S,6R,12aR)-2,3,6,7,12,12a-hexahydro-6-(5-benzofuranyl)-2,3-dimethylpyrazino[2',1':6,1]pyrido [3,4-b]indole-1,4-dione; (6R,12aR)-2,3,6,7,12,12a-hexahydro-6-(5-benzofuranyl)-2-isopropyl-pyrazino [2',1':6,1]pyrido[3,4-b]indole-1,4-dione; and physiologically acceptable solvates (e.g. hydrates) thereof.

A most particular compound useful in this invention is (6R,12aR)-2,3,6,7,12,12a-hexahydro-6-(5-benzofuranyl)-2-methyl-pyrazino[2',1':6,1]pyrido[3,4-b]indole-14-dione; and physiologically acceptable solvates (e.g. hydrates) thereof.

The term "halogen" as used herein denotes bromine, chlorine, fluorine and iodine. The terms "C1–3alkyl" and "C1–6alkyl" as used herein denote a straight or branched alkyl chain such as methyl, ethyl, i-propyl, n-butyl, pentyl, hexyl or the like.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

Compounds useful in the methods of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

For administration to humans in the curative or prophylactic treatment of the disorders identified above, oral dosages of a compound of Formula I will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice, the physician will determine the actual dosing regimen that will be most suitable for an individual patient and it will vary with the age, weight and response of the particular patient. The above dosages are believed to be exemplary of the average case, but there may be individual instances in which higher or lower dosage ranges may be merited, and such are within the scope of this invention.

Compounds of Formula I may be prepared by any suitable method known in the art or by the following processes that are set forth in PCT/EP96/03025. In the methods below, $R_0$, $R_1$, $R_2$, and $R_3$ are as defined in Formula I above, unless otherwise indicated.

A first process (A) for preparing a compound of Formula I comprises treating a compound of Formula II

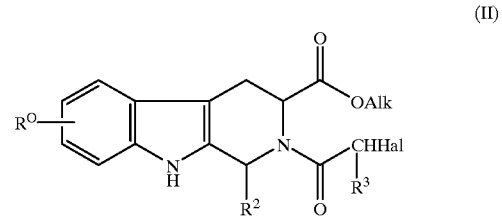

(II)

(in which Alk represents C1–6 alkyl, e.g. methyl or ethyl, and Hal is a halogen atom, e.g. chlorine) with a primary amine $R_1NH_2$ in a suitable solvent such as an alcohol (e.g. methanol or ethanol) or a mixture of solvents, conveniently at a temperature of from 200C. to reflux (e.g. at about 500C.).

According to a second process (B) for preparing a compound of Formula I comprises hydrogenating a compound of Formula III

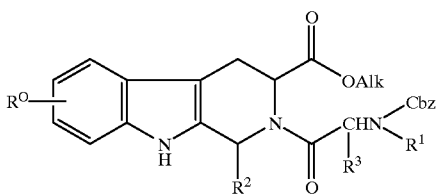

(III)

in which Alk is defined as above and Cbz represents a carbobenzyloxy group, in the presence of a catalyst (e.g. palladium on activated carbon) in a suitable solvent such as an alcohol, e.g. methanol or ethanol, at elevated temperature, A compound of Formula II may conveniently be prepared by treating a compound of Formula IV

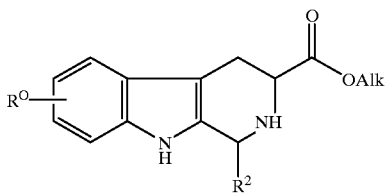

(IV)

with a haloacetyl halide (e.g. chloroacetyl chloride) in a suitable solvent such as a halogenated hydrocarbon (e.g. trichloromethane or dichloromethane), or an ether (e.g. tetrahydrofuran), preferably in the presence of a base such as an organic amine (e.g. a trialkylamine such as triethylamine) or an alkali metal carbonate or bicarbonate (e.g. $NaHCO_3$). The reaction may, conveniently be effected at a temperature of from $-20°$ C. to $+200°$ C. (e.g. at about $0°$ C.).

A compound of Formula IV may conveniently be prepared from a tryptophan alkyl ester of Formula V

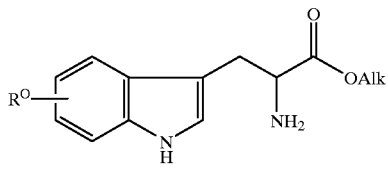

(V)

This step comprises a Pictet-Spengler cyclization between a compound of Formula V and an aldehyde $R_2CHO$. The reaction may conveniently be effected in a suitable solvent such as a halogenated hydrocarbon (e.g. dichloromethane) or an aromatic hydrocarbon (e.g. toluene) in the presence of an acid such as trifluoroacetic acid. The reaction may conveniently be carried out at a temperature of from $-200°$ C. to reflux to provide a compound of Formula III in one step. The reaction may also be carried out in a solvent such as an aromatic hydrocarbon (e.g. benzene or toluene) under reflux, optionally using a Dean-Stark apparatus to trap the water produced. The reaction provides a mixture of cis and trans isomers which may, be either individual enantiomers or racemates of pairs of cis or trans isomers depending upon whether racemic or enantiomerically pure trytophan alkyl ester was used as the stating material. Individual cis or trans enantiomers may conveniently be separated from mixtures thereof by fractional crystallization or by chromatography (e.g. flash column chromatography) using appropriate solvents and eluents. Similarly, pairs of cis and trans isomers may be separated by chromatography (e.g., flash column chromatography) using appropriate eluents.

An optically pure trans isomer may also be converted to an optically pure cis isomer using suitable epimerization procedures. One such procedure comprises treating the trans isomer or a mixture (e.g., a 1:1 mixture) of cis and trans isomers with methanolic or aqueous hydrogen chloride at a temperature of from $0°$ C. to the refluxing temperature of the solution. The mixture is then subjected to chromatography (e.g., flash column chromatography) to separate the resulting diastereoisomers.

A compound of Formula III may be prepared by reaction of a compound of Formula IV as described above, with a compound of Formula VI

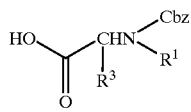

(VI)

wherein Cbz is defined above. Suitably, the reaction is carried out in the presence of 1,3-dicyclohexyl carbodiimide (DCC), in a solvent such as halogenated hydrocarbon (e.g., dichloromethane) from $0°$ C. to room temperature.

Compounds of Formula V and VI are known compounds or may be prepared by standard methods described below.

Compounds useful in this invention may be isolated in association with solvent molecules by crystallization from or evaporation of an appropriate solvent.

Thus, a process (C) for preparing a compound of Formula I or a solvate (e.g. hydrate) thereof comprises process (A) or (B) as hereinbefore described followed by
 i) an interconversion step; and/or
 ii) solvate (e.g. hydrate) formation.

The synthesis of the compounds useful in this invention and of the intermediates for use in making those compounds are illustrated by the following, non-limiting Examples from the above PCT Application.

INTERMEDIATES 1 and 2

(1R,3R)-Methyl 1,2,3,4-Tetrahydro-1-(5-Benzofuranyl)-9H-Pyrido[3,4-b]Indole-3-Carboxylate, Cis Isomer;

and (1S,3R)-Methyl-1,2,3,4-Tetrahydro-1-(5-Benzofuranyl)-9H-Pyrido[3,4-b]Indole-3-Carboxylate Trans Isomer To a stirred solution of D-tryptophan methyl ester (3.73 g) and 5-formylbenzofuran (2.5 g) (prepared as is described in Chimie Therapeutique 4, pp 221–227 (1966)) in anhydrous dichloromethane (100 ml) cooled at $0°$ C. was added dropwise trifluoroacetic acid (2.63 ml), and the solution was allowed to react at ambient temperature. After 72 hours, the solution was washed with a saturated aqueous solution of $NaHCO_3$, then with water and dried over $Na_2SO_4$. The organic layer was evaporated under reduced pressure, and the residue was purified by flash chromatography eluting with dichloromethane/ethyl acetate (90/10) to give first the cis isomer (Intermediate 1) (3 g) as an amorphous compound, followed by the trans isomer (intermediate 2) (2.5 g) as white crystals, m.p.: 194–195° C.

INTERMEDIATE 3

(1R,3R)-Methyl 1,2,3,4-Tetrahydro-1-(5-Benzofuranyl)-2-Chloroacetyl-9H-Pyrido[3,4-b]Indole-3-Carboxylate To a stirred solution of Intermediate 1 (2 g) and triethylamine (0.88 ml) in anhydrous dichloromethane (40 mL)

cooled at 0° C. was added dropwise chloroacetylchloride (0.5 ml), and the solution was stirred at the same temperature for 1 hour. The solution was washed with water, dried over $Na_2SO_4$ and evaporated to dryness, and the residue was crystallized from methanol to give the title compound (1.8 g) as pale yellow crystals. m.p.: 227–228° C.

INTERMEDIATE 4

(1R,3R)-Methyl 1,2,3,4-Tetrahydro-1-(5-Benzofuranyl)-2-(2-(S)-Benzyloxycarbonylaminopronionyl)-9H-Pyrido[3,4-b]Indole-3-Carboxylate To a stirred solution of (S)-2-benzyloxycarbonylaminopropionic acid (1.3 g) and 1,3-dicyclohexyl carbodiimide (DCC) (1.2 g) in anhydrous dichloromethane (50 ml) at 0° C. was added Intermediate 1 (1.0 g). The resulting mixture was stirred for 72 hours then the resulting precipitate filtered off. The filtrate was evaporated to dryness and the residue purified by flash chromatography, eluting with cyclohexane/ethyl acetate (60/40) to give the title compound as white crystals (1.4 g) m.p.: 91–92° C.

INTERMEDIATE 5

(1R,3R)-Methyl 1,2,3,4-Tetrahydro-1-(5-Benzofuranyl)-2-[2-(S)-Benzyloxycarbonylmethylamino)Propionyl]-9H-Pyrido[3,4-b]Indole-3-Carboxylate The same procedure employed in the preparation of Intermediate 4 but starting from 2-(S)-benzyloxycarbonylmethylamino)propionic acid (0.82 g) and using Intermediate 1 (0.6 g), DCC (0.72 g) and dichloramethane (25 ml) gives after chromatography, eluting with cyclohexane/ethyl acetate (70/30), the title compound as a white foam.

EXAMPLE 1

(6R,12aR)-2,3,6,7,12,12a-Hexahydro-6-(5-Benzofuranyl)-2-Methyl-Pyrazino[2',1':6,1]Pyrido[3,4-b]Indole-1,4-Dione To a stirred suspension of Intermediate 3 (0.42 g) in methanol (30 ml) is added at ambient temperature a solution of methylamine (33% in ETOH) (0.47 ml), and the resulting mixture is heated at 50° C. under $N_2$ for 72 hours. The solvent is removed under reduced pressure and dissolved in dichloromethane. After washing with water, drying over $Na_2SO_4$ and evaporating to dryness, the crude product is purified by crystallization from methanol to give the title compound as white crystals (0.21 g).

m.p.: 291–293° C. Analysis for $C_{23}H_{19}N_3O_3$: Calculated: C, 71.68; H, 4.97; N, 10.90; Reported: C, 71.5; H, 4.91; N, 10.74%. $[\alpha]^{20}_D=+55.7'$ (C=I; $CHCl_3$).

EXAMPLE 2

(6R,12aR)-2,3,6,7,12,12a-Hexahydro-6-(5-Benzofuranyl)Pyrazino[2',1':6,1]Pyrido[3-4-b]Indole-1,4-Dione The same procedure as employed in the preparation of Example I but starting from ammonia and Intermediate 3 gives, after recrystallization from methanol, the title compound as white crystals. m.p.:310–311° C.

Analysis for $C_{22}H_{17}N_3O_3$ (0.4 MEOH): Reported: C, 70.03; H, 4.88; N, 10.94; Found: C, 70.01; H, 4.8; N, 10.61%; $[\alpha]^{20}_D=+60.4-$ (C=0.5; pyridine).

EXAMPLE 3

(6R,12aR)-2,3,6,7,12,12a-Hexahydro-6-(5-Benzofuranyl)-2-Isopropyl-Pyrazino[2',1':6.1]Pyrido[3,4-B]Indole-1,4-Dione The same procedure as employed in the preparation of Example 1 but starting from isopropylamine and Intermediate 3 gave, after recrystallisation from methanol, the title compound as white crystals.

m.p.: 291–292° C. Analysis for $C_{25}H_{23}N_3O_3$ (0.6 MeOH): Calculated: C, 71.06; H, 5.92; N, 9.71; Found: C, 70.94; H, 5.62; N, 9.77%. $[\alpha]^{20}_D=+37.9°$ (C=I; CHCI3).

EXAMPLE 4

(3S,6R,12aR)-2,3,6,7,12,12a-Hexahydro-6-(5-Benzofuranyl)-3-Methyl-Pyrazino[2',1':6,1]Pyrido[3,4-b]Indole-1,4-Dione A solution of Intermediate 4 (0.3 g) in the presence of 10%Pd/C (30 mg) in methanol (10 ml) is stirred under an atmosphere of hydrogen at 50° C. for two hours. The reaction mixture is cooled, filtered through Celite, the filter cake washed with methanol and the filtrate evaporated in vacuo. The residue was purified by flash chromatography, eluting with dichloromethane/methanol (98/2) to give the title compound as white crystals after recrystallization from methanol (0.15 g).

m.p.: 150–151° C. Analysis for $C_{23}H_{19}N_3O_3$ (0.1 MeOH) Calculated: C, 71.39; H, 5.03; N, 10.81; Found: C, 71.08; H, 5.16; N, 10.50%; $[\alpha]^{20}_D=+50-$ (C=0.25; $CHCl_3$).

EXAMPLE 5

(3S,6R,12aR)-2,3,6,7,12,12a-Hexahydro-6-(5-Benzofuranyl)-3-Methyl-Pyrazino[2',1':6,1]Pyrido[3,4-b]Indole-1,4-Dione The same procedure as employed in the preparation of Example 4 but starting from Intermediate 5 (0.52 g) and using 10%Pd/C (50 mg) in methanol (20 ml) gave. after recrystallization from methanol, the title compound as white crystals (40 mg).

m.p.: 323–324° C. Analysis for $C_{24}H_{21}N_3O_3$. (0.1 Methanol) Calculated: C, 71.52; H, 5.35; N, 10.43; C, 71.71; H, 5.44; N, 10.39%; $[\alpha]^{20}_D=+53'$ (C=0.35; $CHCl_3$)-

It will be understood that various changes and modifications can be made in the details of procedure, formulation and use without departing from the spirit of the invention, especially as defined in the following claims.

We claim:

1. A method of treating a mammal having precancerous lesions sensitive to such a compound comprising administering to said mammal a pharmacologically effective amount of a compound of Formula I or pharmaceutically acceptable salt thereof:

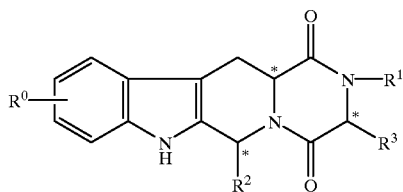

(I)

wherein

R₀ represents hydrogen, halogen or C1–6 alkyl;

R₁ represents hydrogen or C1–6alkyl;

R₂ represents the bicyclic ring

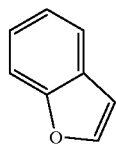

which may be optionally substituted by one or more groups selected from halogen and C1–3 alkyl; and R₃ represents hydrogen or C1–3alkyl.

2. The method of claim 1 wherein R₀ represents hydrogen.

3. The method of claim 2 wherein R₁ is selected from hydrogen, methyl, and isopropyl.

4. The method of claim 3 wherein R₃ represents hydrogen or methyl.

5. The method of claim 1 wherein said compound is selected from the group consisting of (6R,12aR)-2,3,6,7,12,12a-Hexahydro-6-(5-benzofuranyl)-2-methyl-pyrazino[2',1':6,1]pyrido[3,4-b]indole-1,4-dione; (6R,12aR)-2,3,6,7,12,12a-Hexahydro-6-(5-benzofuranyl)-pyrazino[2',1':6,1]pyrido[3,4-b]indole-1,4-dione; (3S,6R,12aR)-2,3,6,7,12,12a-Hexahydro-6-(5-benzofuranyl)-3-methylpyrazino[2',1':6,1]pyrido [3,4-b]indole-1,4-dione; (3S,6R-12aR)-2,3,6,7,12,12a-Hexahydro-6-(5-benzofuranyl)-2,3 -dimethyl-pyrazino[2',1':6,1]pyrido[3,4-b]indole-1,4-dione; and (6R,12aR)-2,3,6,7,12,12a-Hexahydro-6-(5-benzofuranyl)-2-isopropylpyrazino[2',1':6,1]pyrido[3,4-b]indole-1,4-dione, and physiologically acceptable solvates thereof.

6. The method of claim 1 wherein said compound is selected from (6R,12aR)-2,3,6,7,12,12a-Hexahydro-6-(5-benzofuranyl)-2-methyl-pyrazino[2'.1':6,1]pyrido[3,4-b]indole-1,4-dione and physiologically acceptable solvates thereof.

7. A method for inhibiting the growth of neoplastic cells comprising exposing the cells sensitive to such a compound to a growth inhibiting effective amount of a compound of Formula I or pharmaceutically acceptable salt thereof:

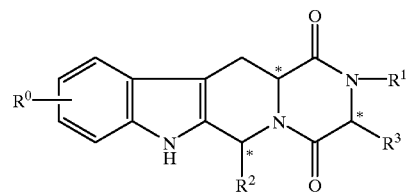

(I)

wherein

R₀ represents hydrogen, halogen or C1–6 alkyl;

R₁ represents hydrogen or C1–6alkyl;

R₂ represents the bicyclic ring

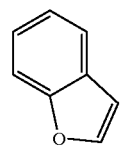

which may be optionally substituted by one or more groups selected from halogen and C1–3 alkyl; and R₃ represents hydrogen or C1–3alkyl.

8. The method of claim 6 wherein R₀ represents hydrogen.

9. The method of claim 7 wherein R₁ is selected from hydrogen, methyl, and isopropyl.

10. The method of claim 8 wherein R₃ represents hydrogen or methyl.

11. The method of claim 6 wherein said compound is selected from the group consisting of (6R,12aR)-2,3,6,7,12,12a-Hexahydro-6-(5-benzofuranyl)-2-methyl-pyrazino[2',1:6,1]pyrido[3,4-b]indole-1,4-dione; (6R,12aR)-2,3,6,7,12,12a-Hexahydro-6-(5-benzofuranyl)-pyrazino[2',1':6,1]pyrido[3,4-b]indole-1,4-dione; (3S,6R,12aR)-2,3,6,7,12,12a-Hexahydro-6-(5-benzofuranyl)-3-methylpyrazino[2',1':6,1]pyrido [3,4-b]indole-1,4-dione; (3S,6R,12aR)-2,3,6,7,12,12a-Hexahydro-6-(5-benzofuranyl)-2,3-dimethyl-pyrazino[2',1':6,1]pyrido[3,4-b]indole-1,4-dione; and (6R,12aR)-2,3,6,7,12,12a-Hexahydro-6-(5-benzofuranyl)-2-isopropyl-pyrazino[2',1':6,1]pyrido[3,4-b]indole-1,4-dione; and physiologically acceptable solvates thereof.

12. The method of claim 6 wherein said compound is selected from (6R,12aR)-2,3,6,7,12,12a-Hexahydro-6-(5-benzofuranyl)-2-methyl-pyrazino[2'.1':6,1]pyrido[3,4-b]indole-1,4-dione and physiologically acceptable solvates thereof.

* * * * *